US008563043B2

(12) United States Patent
Medarova et al.

(10) Patent No.: US 8,563,043 B2
(45) Date of Patent: Oct. 22, 2013

(54) INNATELY MULTIMODAL NANOPARTICLES

(75) Inventors: Zdravka Medarova, Methuen, MA (US); Anna Moore, Dracut, MA (US); Mehmet Yigit, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/142,730

(22) PCT Filed: Mar. 16, 2010

(86) PCT No.: PCT/US2010/027406
§ 371 (c)(1),
(2), (4) Date: Jun. 29, 2011

(87) PCT Pub. No.: WO2010/111066
PCT Pub. Date: Sep. 30, 2010

(65) Prior Publication Data
US 2012/0004531 A1    Jan. 5, 2012

Related U.S. Application Data

(60) Provisional application No. 61/162,487, filed on Mar. 23, 2009.

(51) Int. Cl.
*A61K 9/14*    (2006.01)
(52) U.S. Cl.
USPC .......................................... 424/489; 424/490
(58) Field of Classification Search
None
See application file for complete search history.

(56) References Cited

U.S. PATENT DOCUMENTS

| 2005/0130167 | A1 | 6/2005 | Bao et al. | |
| 2006/0234248 | A1* | 10/2006 | Sun et al. | 435/6 |
| 2008/0057001 | A1 | 3/2008 | Sun | |
| 2008/0095714 | A1* | 4/2008 | Castella et al. | 424/9.3 |

FOREIGN PATENT DOCUMENTS

| EP | 1710811 A2 | 10/2006 |
| EP | 1852107 | 11/2007 |
| WO | 2007117572 A2 | 10/2007 |

OTHER PUBLICATIONS

The International Search Report and Written Opinion as mailed on Oct. 26, 2010 for International Application No. PCT/US2010/027406.
Ban, et al., The Synthesis of Core-Shell Iron@Gold Nanoparticles and Their Characterization, Journal of Materials Chemistry, 2005, 15:4660-4662.
Cho, et al., Gold-Coated Iron Nanoparticles: A Novel Magnetic Resonance Agent for T1 and T2 Weighted Imaging, Nanotechnology, 2006, 17:640-644.
De La Fuente, et al., Gold and Gold-Iron Oxide Magnetic Glyconanoparticles: Synthesis, Characterization and Magnetic Properties, The Journal of Physical Chemistry B, 2006, 110:13021-13028.
Harisinghani, et al., Noninvasive Detection of Clinically Occult Lymph-Node Metastases in Prostate Cancer, The New England Journal of Medicine, 2003, 348:2491-2499.
Kim, et al., Designed Fabrication of Multifunctional Magnetic Gold Nanoshells and Their Application to Magnetic Resonance Imaging and Photothermal Therapy, Angewandte Chemie International Ed., 2006, 45:7754-7758.
Kouassi, et al., Magnetic and Gold-Coated Magnetic Nanoparticles as a DNA Sensor, Analytical Chemistry, 2006, 78:3234-3241.
Kouassi, et al., Aptamer-Mediated Magnetic and Gold-Coated Magnetic Nanoparticles as Detection Assay for Prion Protein Assessment, Biotechnology Progress, 2007, 23:1239-1244.
Lee, et al., Dextran-Gold Nanoparticle Hybrid Material for Biomolecule Immobilization and Detection, Analytical Chemistry, 2005, 77(22):7204-7211.
Mandal, et al., Magnetite Nanoparticles with Tunable Gold or Silver Shell, Journal of Colloid and Interface Science, 2005, 286:187-194.
Melancon, et al., Theragnostics with Magnetic Gold Nanoshells: Photothermal Therapy and T2* Magnetic Resonance Imaging, Proc WMIC 2008.
Park, et al., Fabrication of Magnetic Core@Shell Fe Oxide@Au Nanoparticles for Interfacial Bioactivity and Bio-Separation, Langmuir, 2007, 23:9050-9056.
Pham, et al., Application of Citrate-Stabilized Gold-Coated Ferric Oxide Composite Nanoparticles for Biological Separations, Journal of Magnetism and Magnetic Materials, 2008, 320:2049-2055.
Stoeva, et al., Three-Layer Composite Magnetic Nanoparticle Probes for DNA, Journal of the American Chemical Society, 2005, 127:15362-15363.
Wang, et al., Magnetic Resonance Tracking of Nanoparticle Labelled Neural Stem Cells in a Rat's Spinal Cord, Nanotechnology, 2006, 17:1911-1915.
Xu, et al., Magnetic Core/Shell Fe3O4/Au and Fe3O4/Au/Ag Nanoparticles with Tunable Plasmonic Properties, Journal of the American Chemical Society, 2007, 129:8698-8699.
Zhang, et al., Laser-Assisted Synthesis of Superparamagnetic Fe@Au Core-Shell Nanoparticles, The Journal of Physical Chemistry B, 2006, 110:7122-7128.

* cited by examiner

*Primary Examiner* — Michael G Hartley
*Assistant Examiner* — Robert Cabral
(74) *Attorney, Agent, or Firm* — Quarles & Brady LLP (57) ABSTRACT

A gold-coated iron oxide nanoparticle, method of making thereof, and method of using thereof is disclosed. The nanoparticle is substantially toxin free (making it clinically applicable), easily functionalized, and can serve as a contrast agent for a number of imaging techniques, including imaging a subject in at least two distinct imaging modes. Further, the nanoparticle is well-suited for therapeutic uses.

26 Claims, 13 Drawing Sheets

INNATELY MULTIMODAL NANOPARTICLES

CROSS-REFERENCE TO RELATED APPLICATION

This application represents the national stage entry of PCT international application No. PCT/US2010/027406 filed on Mar. 16, 2010 which claims priority to U.S. provisional patent application Ser. No. 61/162,487 filed on Mar. 3, 2009, the entire contents of which are incorporated herein by reference.

STATEMENT OF FEDERALLY SPONSORED RESEARCH OR DEVELOPMENT

Not applicable.

BACKGROUND OF THE INVENTION

This invention relates to nanoparticles. In particular, this invention relates to nanoparticles that are clinically applicable for diagnostic and/or therapeutic uses.

Medical imaging is used to collect information about a subject. In some types of imaging, a contrast agent is administered to the subject. The contrast agent selectively binds to a bioparticle or other structure of interest in the subject. This contrast agent is then detected using a medical imaging device and the collected information is used to develop an image or the like.

Although much information can be gathered from even a single medical image, multiple imaging techniques are necessary to provide comprehensive quantitative diagnostic information having high spatial and temporal resolution, high sensitivity of detection, and tomographic capability. In the past, this has often meant that multiple contrast agents would need to be administered to a single subject for each performed modality.

Multimodal contrast agents have been developed that are suitable for detection by various types of modalities. These multimodal contrast agents typically include multiple entities that are each detectable by a separate modality. The multiple entities are typically joined together using chemical linkers to make particles that each contain all of the respective multiple entities. However, the chemical linkers often have varying stabilities in cells and tissues or across time, meaning that some of the entities could separate, thus degrading the quality and usefulness of these contrast agents.

To avoid the problems of chemically linking multiple entities together, some have attempted to form contrast agents having a core-shell structure. However, to date, there have been significant problems developing a core-shell structure that can be clinically applied. The currently available particles either require the use of toxic chemicals during synthesis that limit the use of the resultant contrast agent in the human body or possess a morphology that prevents the particles from being effectively functionalized with targeting moieties.

Hence, a need exists for a multimodal contrast agent that is clinically applicable and efficiently functionalized.

SUMMARY OF THE INVENTION

Multimodal nanoparticles and a method of making these nanoparticles are disclosed. Given their structure and the method in which they are made, these nanoparticles may be clinically applicable and efficiently functionalized. The synthesized nanoparticles may facilitate multiple imaging methods and, in some instances, may be used in therapeutic treatment.

A method of forming gold-coated iron oxide nanoparticles is disclosed. The method comprises contacting dextran-coated iron oxide nanoparticles with a gold donating reagent in a citrate solution to form the gold-coated iron oxide nanoparticles.

In some forms, the gold donating reagent may be chloroauric acid.

In other forms, a gold shell may be formed on each of the dextran-coated iron oxide particles to provide gold-coated iron oxide nanoparticles.

In still other forms, the method may further include forming gold nanoparticles from chloroauric acid. At least some of the gold nanoparticles may be deposited onto a surface of the dextran-coated iron oxide nanoparticles to form gold nanoparticle conjugated iron oxide nanoparticles. Additional gold chloride ions may be reduced on the surface of the gold nanoparticle conjugated iron oxide nanoparticles to form the gold-coated iron oxide nanoparticles. Hydroxylamine may used to reduce the additional gold chloride ions. The gold nanoparticle conjugated iron oxide nanoparticle may be separated by magnetic column prior to reducing additional gold chloride ions on the surface of the gold nanoparticle conjugated iron oxide nanoparticle.

The gold-coated iron oxide nanoparticles may be clinically applicable and may be substantially free of toxins. The gold-coated iron oxide nanoparticles may be MRI active due to the iron oxide and may be CT active due to an amount and morphology of gold surrounding the iron oxide.

The method may also include functionalizing the gold-coated iron oxide nanoparticles with at least one of a Raman spectroscopy active dye and a targeting moiety. By functionalizing the nanoparticles with a Raman spectroscopy active dye, such as DTTC, the nanoparticles may be made SERS active.

A gold-coated iron oxide nanoparticle may be manufactured by the methods described herein.

A nanoparticle is also disclosed which includes an iron oxide core, a dextran layer surrounding the iron oxide core, and a gold coating formed on the dextran layer.

The iron oxide core may be superparamagnetic.

The nanoparticle may have a diameter in a range of about 60 nanometers to about 120 nanometers.

The nanoparticle may have many uses. The nanoparticle may be clinically applicable and may be substantially free of toxins. The nanoparticle may be adapted for use as a contrast agent, for use in a therapeutic application, or for both.

In some forms, the gold coating of the nanoparticle may be functionalized with targeting moieties. The gold coating may be functionalized with a Raman spectroscopy active dye, such as DTTC, or a targeting moiety. The gold coating may be a gold shell surrounding the dextran layer and the iron oxide core.

A method of imaging a subject is also disclosed. The method includes introducing the nanoparticles described herein into a subject and performing at least two modes of imaging in the subject using the nanoparticles as a contrast agent for modes of imaging. The modes of imaging may include two or more of magnetic resonance imaging, CT imaging, and Raman spectroscopy.

A method of providing a therapeutic treatment to a subject is also disclosed. The method includes introducing nanoparticles as described herein into a subject and applying an energy source to raise a temperature of the nanoparticles in the subject. As the temperature of the nanoparticles is increased, a therapeutic treatment is provided to the subject. In some forms, the energy source may be an alternating magnetic field or an infrared light.

Furthermore, the methods of imaging and treatment may be combined as a single method. The nanoparticles used to perform these methods may be manufactured by the methods described herein.

These and still other advantages of the invention will be apparent from the detailed description and drawings. What follows is merely a description of some preferred embodiments of the present invention. To assess the full scope of the invention the claims should be looked to as the preferred embodiments are not intended to be the only embodiments within the scope of the claims.

DETAILED DESCRIPTION OF THE PREFERRED EMBODIMENTS

Figure 1:
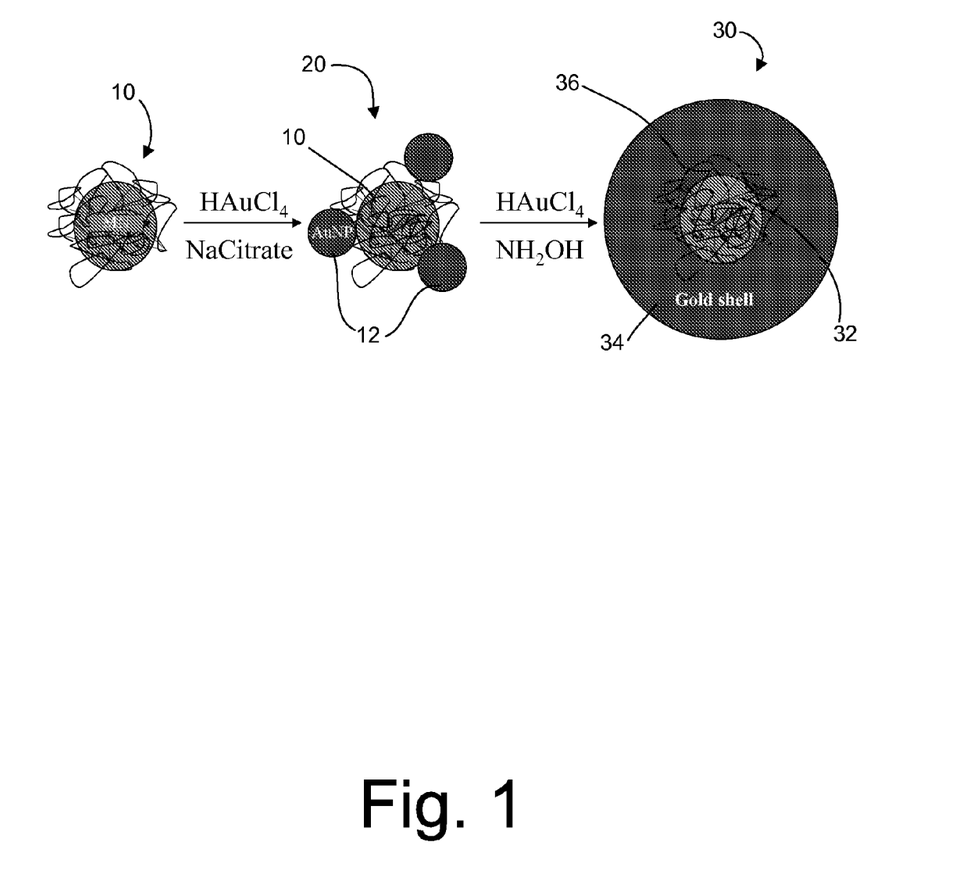
FIG. 1 is a process diagram showing the formation of a gold-coated iron oxide nanoparticle.

Referring first to FIG. 1, a process for forming a gold-coated iron oxide nanoparticle is shown. According to this process, a dextran-coated iron oxide nanoparticle 10 is provided (the dextran coating being indicated by the lines surrounding the sphere in FIG. 1). The dextran-coated iron oxide nanoparticle 10 is exposed to a gold donating reagent in a citrate solution. In one form, and according to the particular process shown in FIG. 1, the gold donating reagent is chloroauric acid ($HAuCl_4$) and the citrate solution is sodium citrate.

Given the conditions in the solution, which may include the application of heat, stirring, or the like as will be described in more detail in the example below, the gold donating reagent forms gold nanoparticles 12 in solution, such as those seen in the TEM of FIG. 2.

While in the citrate solution, some of the formed gold nanoparticles 12 further get deposited onto the dextran-coating on the iron oxide nanoparticle 10, serving as seeds for the formation of a gold nanoparticle conjugated iron oxide nanoparticle 20 upon reduction by citrate. Such attachment or conjugation through dextran is notable because the pairing of magnetic particles, such as iron oxide nanoparticles, with gold has been deemed difficult given the dissimilar nature of the two surfaces.

Next, the gold nanoparticle conjugated iron oxide nanoparticles 20 are separated from the excess of unconjugated gold nanoparticles in the solution. In one form, this separation of the gold nanoparticle conjugated iron oxide nanoparticles 20 from the unconjugated gold nanoparticles is performed by magnetic column. This is possible because of the differing magnetic properties of the unconjugated gold nanoparticles from the gold nanoparticle conjugated iron oxide nanoparticles in the solution.

In the next step, gold ions are reduced on the surface of the separated gold nanoparticle conjugated iron oxide nanoparticles to form a gold shell about the dextran-coated iron oxide nanoparticle. This is done by the subsequent addition of a gold donating reagent (in the form shown, chloroauric acid) and a reducing agent (in the form shown, hydroxylamine, $NH_2OH$). Gold ions from the gold donating reagent are deposited on the surface of the conjugated nanoparticle, beginning the growth of a gold shell around the dextran coated iron oxide nanoparticle. As the deposition continues, a gold-coated iron oxide nanoparticle 30 is formed.

Again, the gold-coated iron oxide nanoparticles 20 are separated from the solution by using a magnetic column technique or the like.

The resultant gold-coated iron oxide nanoparticle 30 has an iron oxide core 32, a surrounding gold shell 34 that substantially surrounds the iron oxide core 32, and an intermediate dextran T-10 layer 36. In one form, the iron oxide core 32 is a mixture of magnetite and maghemite and has a 3-5 nm size. Including the dextran layer 36, the diameter of the dextran-coated iron oxide nanoparticle is in a range of 10-30 nm. After the deposition of gold onto the surface to form the gold shell 34, the final diameter is in the range of 30-120 nm. These values are merely representative of some of the size ranges of the gold-coated iron oxide nanoparticle 30 and its associated elements. By altering the processing variables, it is contemplated that different sizes of nanoparticles could be formed.

The iron oxide core 32 is superparamagnetic, meaning that the core as a whole is not magnetized unless it is subjected to an external magnetic field, and can be detected during, for example, magnetic resonance imaging and the like.

The gold shell 34 is well adapted for functionalization with targeting moieties such as RGD peptides, aptamers, molecular probes, and the like. It is well known in the art that gold serves as a preferred surface for receiving such targeting moieties. By producing gold-coated iron oxide nanoparticles 30 having a gold shell 34 that entirely or substantially covers the iron oxide core 32, the exposed gold surface area for functionalization is maximized meaning the nanoparticles can be efficiently functionalized. In comparison, a particle morphology in which the exposed surface of the particle was not entirely gold would exhibit unpredictable or inefficient attachment of targeting moieties.

As to the applications of the nanoparticle, the gold-coated iron oxide nanoparticle 30 can be detected using three separate imaging modalities—magnetic resonance imaging, computed tomography, and Raman microscopy without the conjugation of additional imaging labels for each of the modalities. This means that the multimodal properties of the gold-coated iron oxide nanoparticle are innate.

The gold-coated iron oxide nanoparticle 30 can also act as a therapeutic agent. When the gold-coated iron oxide nanoparticle 30 is exposed to infrared light and/or an alternating magnetic field, the nanoparticle 30 generates heat and can mediate thermally-mediated cytotoxicity. If the nanoparticle 30 has been functionalized with an appropriate biomolecule, the application of this heat can be targeted at an area of interest in the subject to which the nanoparticle 30 has been administered for thermotherapy.

It is observed that the various chemicals used to form the gold-coated iron oxide nanoparticle 30 do not compromise the ability of gold-coated iron oxide nanoparticle 30 to be used in the human body. Sodium citrate is a safe, clinically applicable reagent, routinely used by the pharmaceutical and food-production industries. Hydroxylamine is routinely used by the pharmaceutical industry for the synthesis of analgesics, antibiotics, tranquillizers, and the like. By using these chemicals, or other non-toxic chemicals with similar reactivities that will not limit the use of the resultant gold-coated iron oxide nanoparticle 30 in the human body, a clinically applicable particle is provided that is substantially free of toxins.

As used herein, "substantially free of toxins" means that the resultant gold-coated iron oxide nanoparticles have no toxins or levels of toxins, either individually or in aggregate, that are low enough to have little, and preferably no, short-term or long-term effects on the health of the individual to which the nanoparticles have been administered. Factors such as the weight, the body chemistry, and the like of the individual to whom the nanoparticles are administered may need to be taken into account in the determination of how much of a toxin is safe for the individual.

To date, the formation of gold shell—magnetic core structures has required the use of chemicals that rendered the resulting particle unfit for use in humans.

Yet, using the chemicals and the process described herein, the resultant particle is clinically applicable. The use of chloroauric acid, sodium citrate, and hydroxylamine does not restrict the clinical use of the resultant nanoparticle. The dextran layer is also non-toxic and, further, has a stabilizing effect on the iron oxide core and has the potential to act as an additional reducing agent.

Thus, the gold-coated iron oxide nanoparticle 30 represents a versatile platform with an array of potential applications. By functionalizing the gold-coated iron oxide nanoparticle 30 with a targeting moiety specific for chosen cells, tissues or biological processes, one can design many diagnostic and/or therapeutic agents. To the best of our knowledge, this is the first clinically relevant trimodal MRI/CT/optical contrast agent that can be functionalized.

Specific examples of the processes used to form a gold-coated iron oxide nanoparticle are provided below. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLE I

According to one specific example, gold-coated iron oxide nanoparticles were prepared in the following manner.

First, 2 mL of 1% sodium citrate were added into 20 mL of boiling distilled water to form a boiling citrate solution. The solution was stirred in an Erlenmeyer flask on a hot plate to achieve uniformity of the citrate solution. 400 microliters of 50 mM chloroauric acid ($HAuCl_4$) solution and 300 microliters of previously prepared mono-dispersed superparamagnetic iron oxide nanoparticles (9.3 mg/ml of iron) were added to the citrate solution.

Upon the addition of the chloroauric acid and the iron oxide nanoparticles to the citrate solution, the color of the solution changed from colorless, to black, and finally to red. The red color was indicative that gold nanoparticles had formed in the solution. Separation of by magnetic column was then performed to separate the gold nanoparticle conjugated iron oxide nanoparticles from the excess unconjugated gold nanoparticles. The separated conjugated nanoparticles had a reddish-brownish color.

Figure 2:
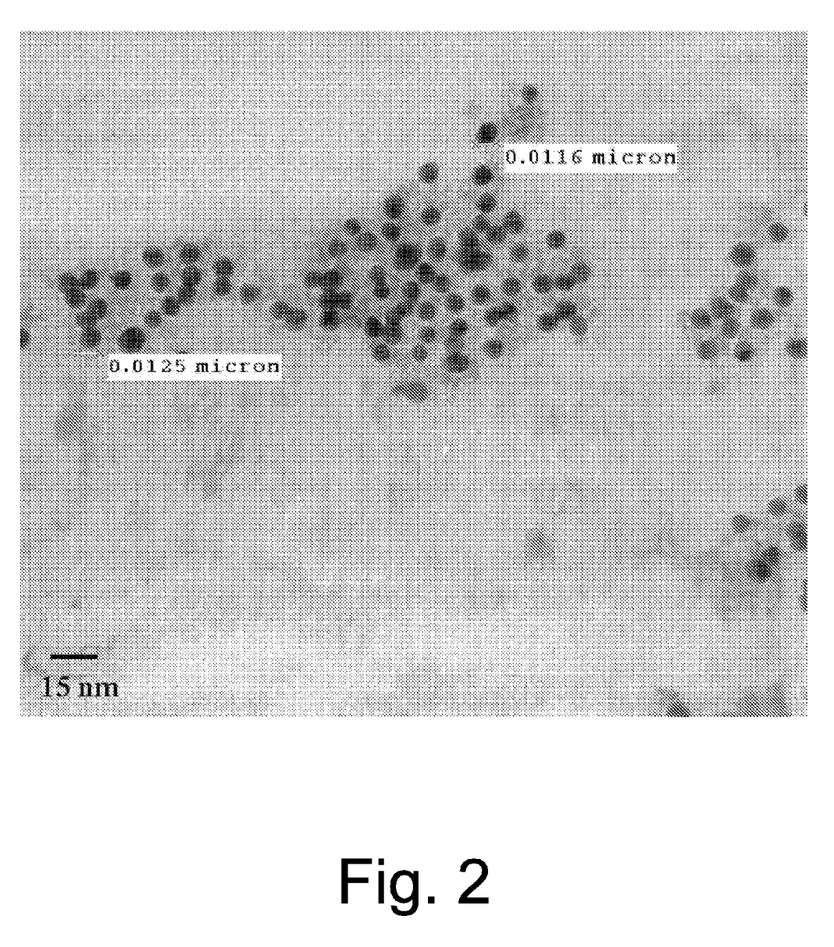
FIG. 2 is a transmission electron microscope (TEM) image of 13 nm gold nanoparticles (AuNP)
Figure 3:
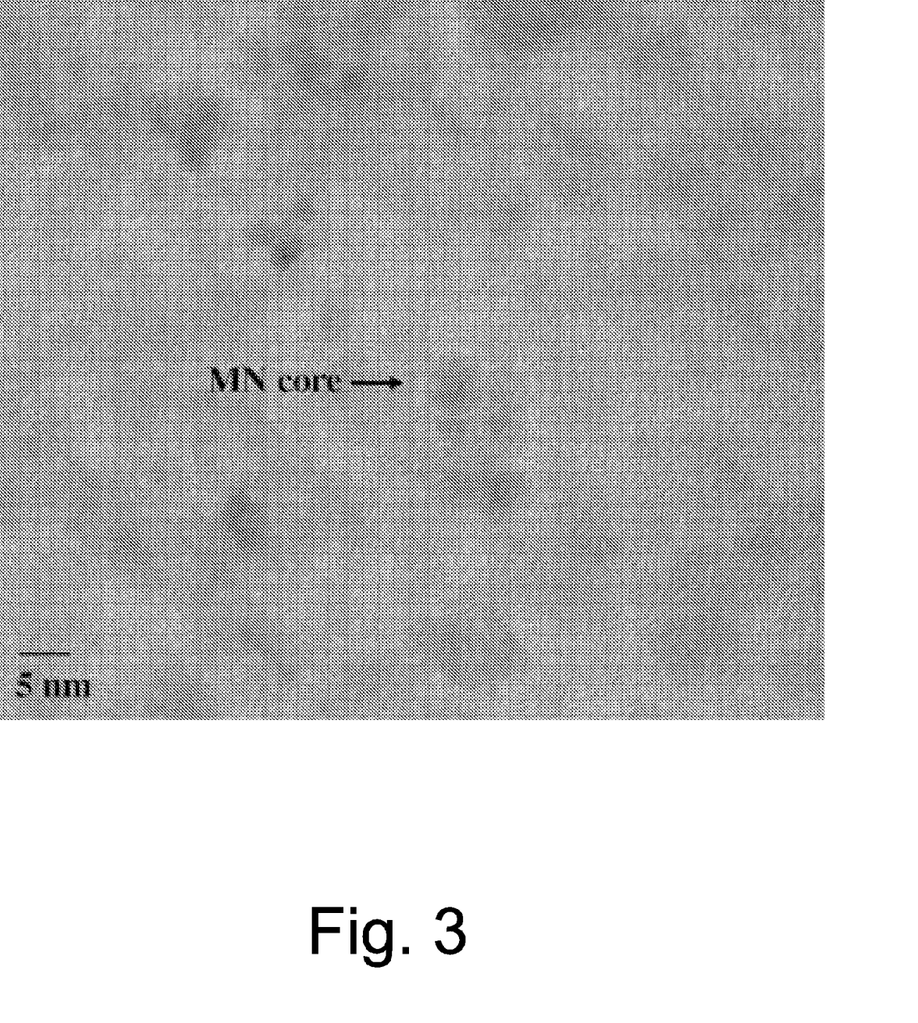
FIG. 3 is a TEM image of a mono-dispersed superparamagnetic iron oxide nanoparticle (MN)

FIG. 2 shows an image made by a transmission electron microscope of the prepared gold nanoparticles and FIG. 3 shows an image of the iron oxide nanoparticle core before conjugation. As visually shown in FIG. 2 and further supported by dynamic light scattering results, the size of the formed gold nanoparticles alone are approximately 13 nm. The size of the iron oxide nanoparticle with the dextran coating is approximately 30 nm and the iron oxide core alone is approximately 5 nm based on the TEM image of FIG. 3.

Figure 4:
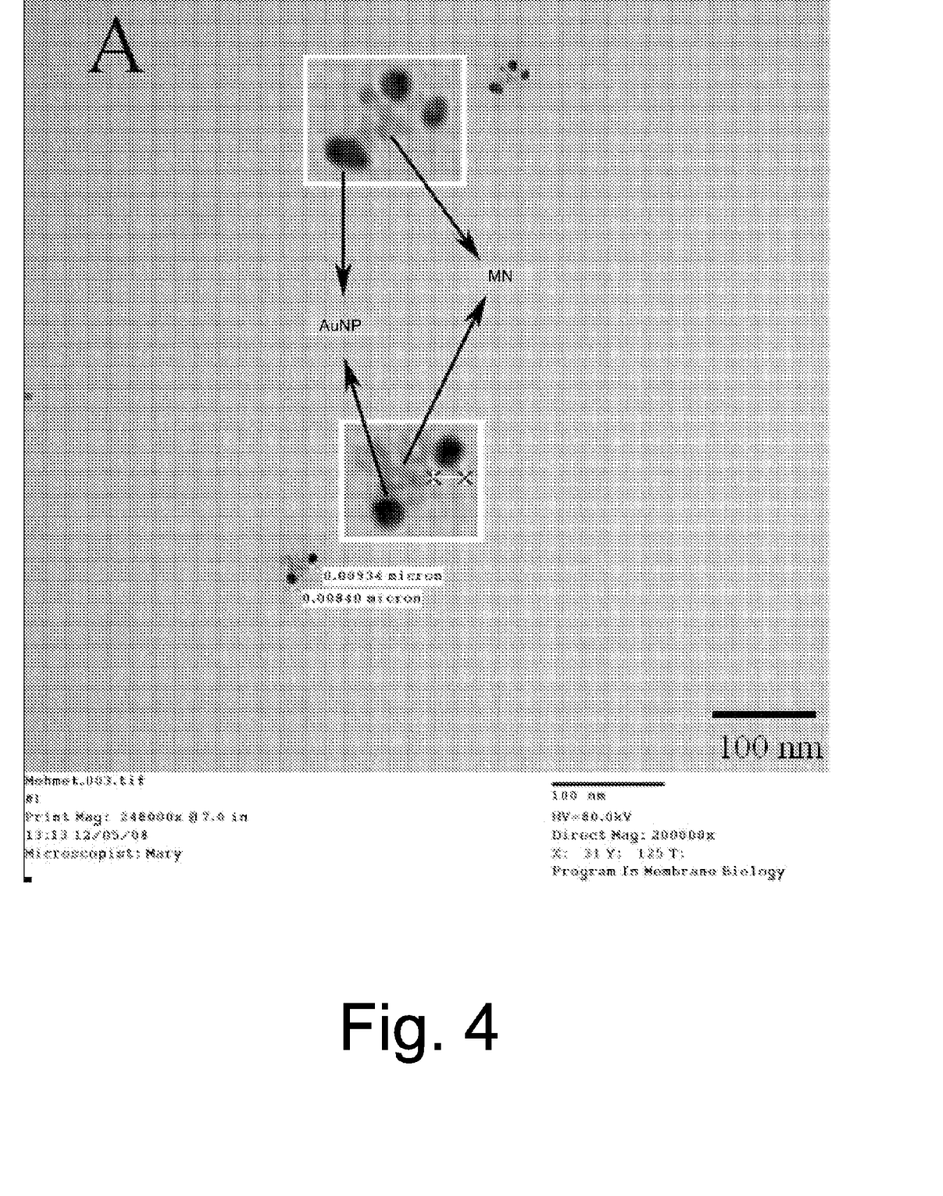
FIG. 4 is a TEM image of AuNP conjugated MNs.
Figure 5:
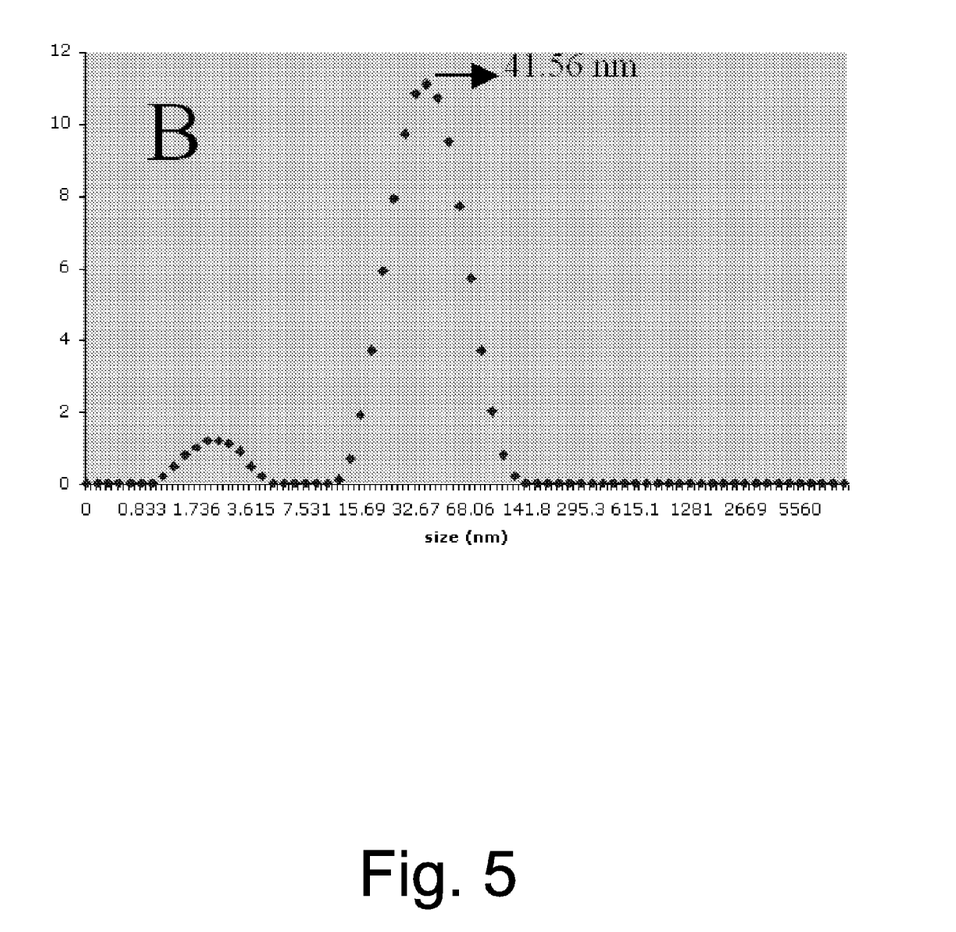
FIG. 5 is a dynamic light scattering graph of AuNP conjugated MNs indicating the size of the particles.

It is believed that after citrate stabilization occurs, the gold nanoparticles begin to attach to the dextran-coated surfaces of the iron oxide nanoparticle. As seen in FIG. 4, a TEM image of the separated gold nanoparticle conjugated iron oxide nanoparticles indicates that the resultant conjugates are approximately 40 nm in size. This image shows numbers of gold nanoparticles attaching to the surface of the dextran coated iron oxide nanoparticle, increasing its size. Gold particle conjugation is further supported by the dynamic light scattering results shown in FIG. 5 which reveal an average particle size in the separated conjugated nanoparticles of 42 nm.

Next, chloroauric acid and hydroxylamine ($NH_2OH$) were introduced to the separated conjugated nanoparticles to further reduce gold ions onto the surface of the conjugated nanoparticle and deposit gold ions to form a gold shell around the iron oxide core. According to the specific process, 2 mL of the gold nanoparticle conjugated iron oxide nanoparticles was mixed with 75 microliters of 1% chloroauric solution. This mixture is stirred at room temperature. Then 150 mM of the hydroxylamine was slowly added in a dropwise fashion to the stirred solution. The color of the solution shifted from the reddish-brownish color to a dark red. After the color change was complete, the dropwise addition of hydroxylamine was halted and the resulting nanoparticle solution was purified by magnetic column against distilled water.

A red colored suspension was recovered from the magnetic column separation. This red color is indicative of a gold surface for the formed particles. However, as the particles were separated by magnetic column, it is clear that the particles were also magnetic.

Figure 6:
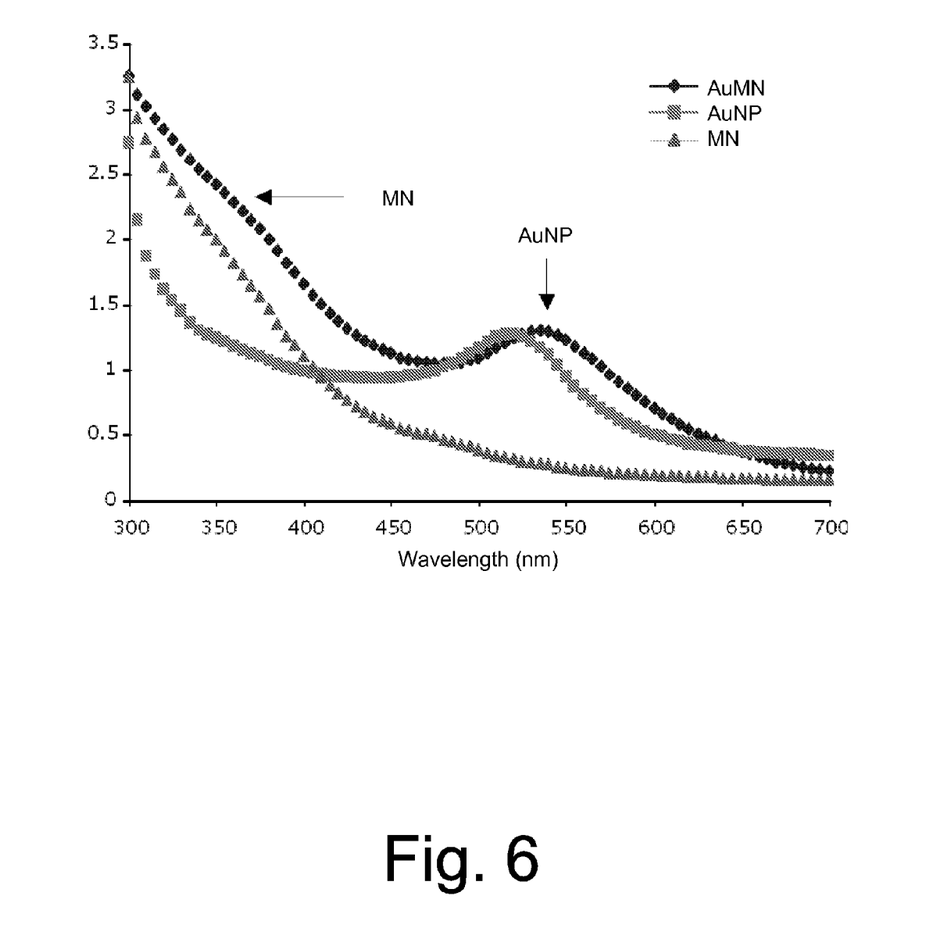
FIG. 6 is a diagram showing the absorbance of gold-coated iron oxide nanoparticles (AuMN), gold nanoparticles (AuNP), and iron oxide nanoparticles (MN)

Referring now to FIG. 6, absorbance of the resulting suspension was determined by UV-vis spectroscopy. This spectrum was compared to known absorbance spectra of the iron oxide nanoparticles and the gold nanoparticles. The measured spectrum of the resulting suspension had a gold nanoparticle plasmon resonance peak, strongly suggesting that the resultant nanoparticle contained gold nanostructures.

Figure 7:
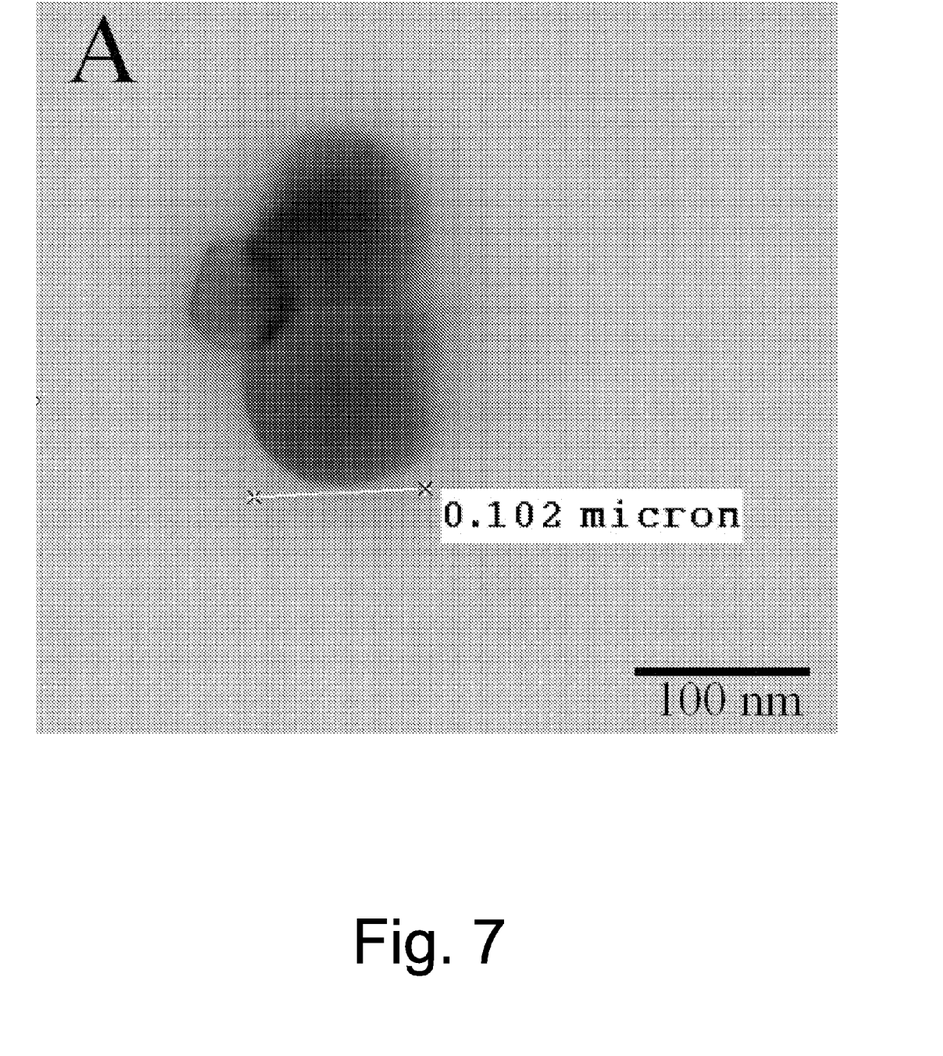
FIG. 7 is a TEM image of a gold-coated iron oxide nanoparticle.
Figure 8:
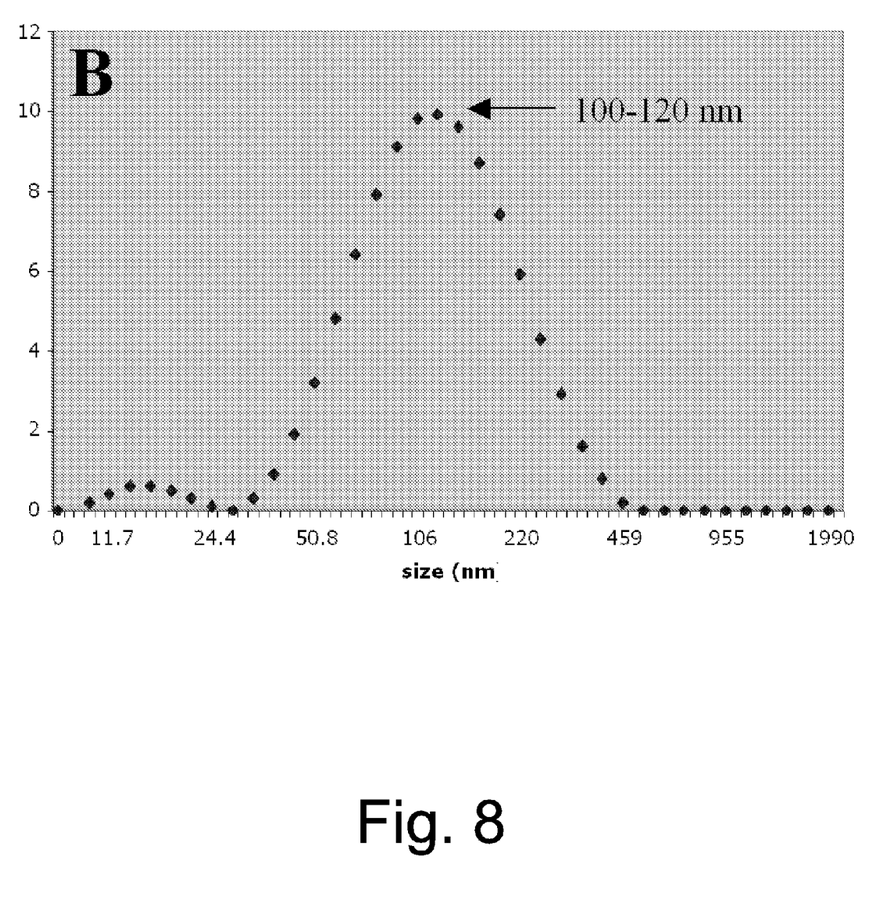
FIG. 8 is a dynamic light scattering graph of the gold-coated iron oxide nanoparticle.

Referring now to FIGS. 7 and 8, the resultant nanoparticles of the suspension were imaged using TEM and measured using dynamic light scattering. Each of these reveal that the resultant nanoparticle size is in the range of 100 to 120 nanometers.

Given the above-collected data, nanoparticles having a gold-shell, iron-oxide core with an intermediate dextran layer were formed. Although a specific example has been provided, it is contemplated that the processing variables could be altered to modify one or more of the characteristics of the resultant particle. For example, it is contemplated that an increase or reduction in the amount of chloroauric acid presented in the reduction step could alter the thickness of the gold shell and the size of the final nanoparticle. Likewise, the temperature of the various solutions could be altered to change the reaction kinetics and resultant nanoparticle structures created therefrom.

EXAMPLE II

According to another example, multilayered nanoparticles AuMN-DTTC, which can be used as a MRI-SERS-CT active contrast agent were also prepared. AuMN-DTTC includes (1) iron oxide, which makes it MRI active-gold, which makes it CT active (2) DTTC (diethylthiatricarbocyanine, a Raman active dye) and (3) gold nanostructures, which makes it SERS active material.

Figure 9:
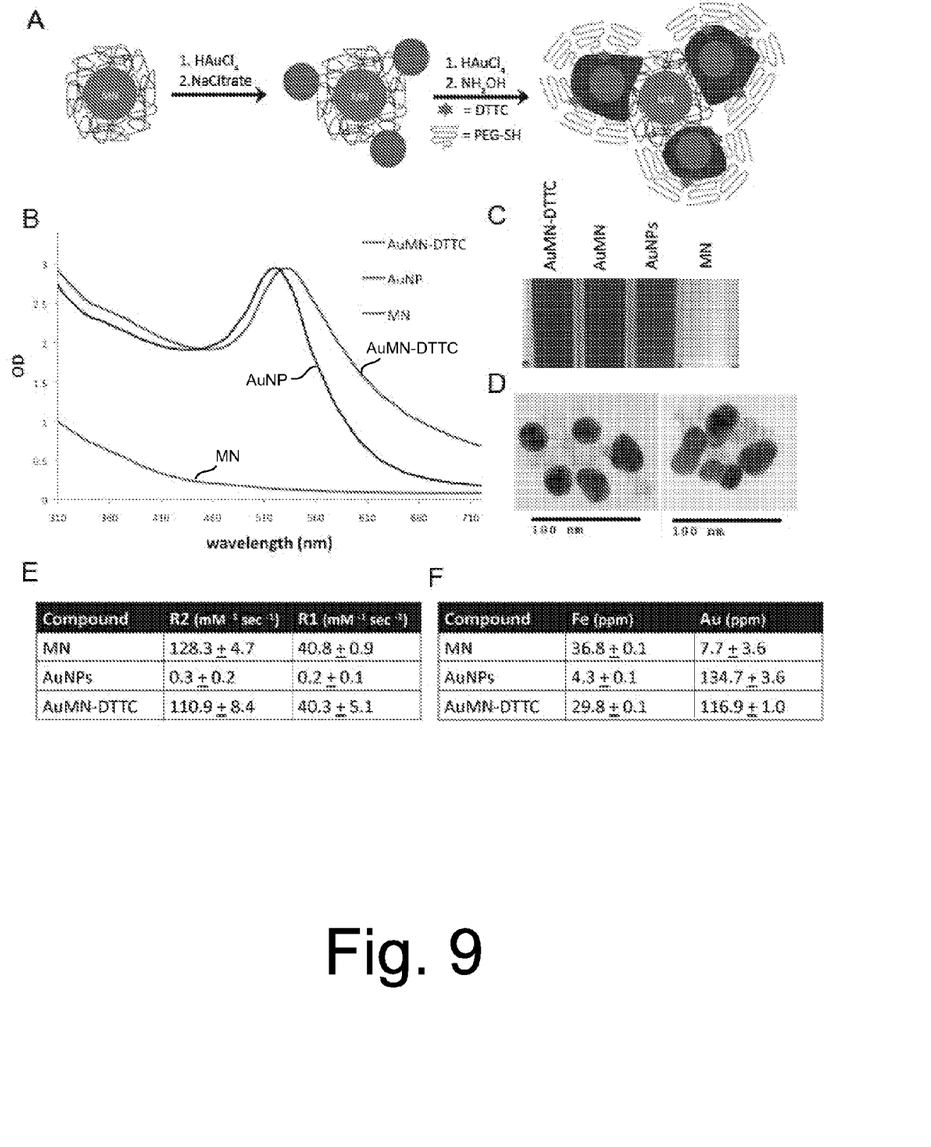
FIG. 9A is a process diagram showing the synthesis of an AuMN-DTTC nanoparticle.
FIG. 9B is dynamic light scattering graph of the AuMN-DTTC and control probes.
FIG. 9C are pictures of AuMN-DTTC and control probe suspensions in cuvettes.
FIG. 9D are pictures of TEM images of AuMN-DTTC.
FIG. 9E is a chart of relaxivity values of the probes.
FIG. 9F is a chart of elemental analysis of the probes.

Referring now to FIG. 9A, a schematic representation of the multi-step synthesis of the contrast agent is illustrated. The process steps are similar to those shown in FIG. 1, but with the addition of DTTC and PEG-SH (polyethylene glycol-thiol or sulfhydryl) during the second step. As can be seen in the resultant product, during the second step, additional gold is reduced on the surface of the gold-conjugated nanoparticles and the DTTC and PEG-SH are attached to the growing Au-nanoparticles. In the form shown, less than a full shell of gold is formed around the magnetic nanoparticle.

FIG. 9B shows the absorbance spectra of AuMN-DTTC, AuNP (gold nanoparticles), and MN (iron oxide nanoparticles) in water. AuMN-DTTC has a surface plasmon resonance peak at 530 nm which is similar to surface plasmon resonance peak at 520 nm of AuNP. MN does not have a corresponding peak, which suggests that the resonance peak in the AuMN-DTTC must be due to presence of gold nanostructures. The dark red color of the AuMN-DTTC in FIG. 9C and the TEM images in FIG. 9D also suggest that the gold nanostructures are present in the composition of the probe.

With additional reference to FIG. 9E, the relaxivity (R1 and R2) values indicate that the validity of AuMN-DTTC as an MRI contrast agent is not too different than the MN, which is a clinically approved MRI contrast agent. As shown in FIG. 9F, elemental analysis on AuMN-DTTC confirms the presence of iron and gold in the composition of the probe.

Figure 10:
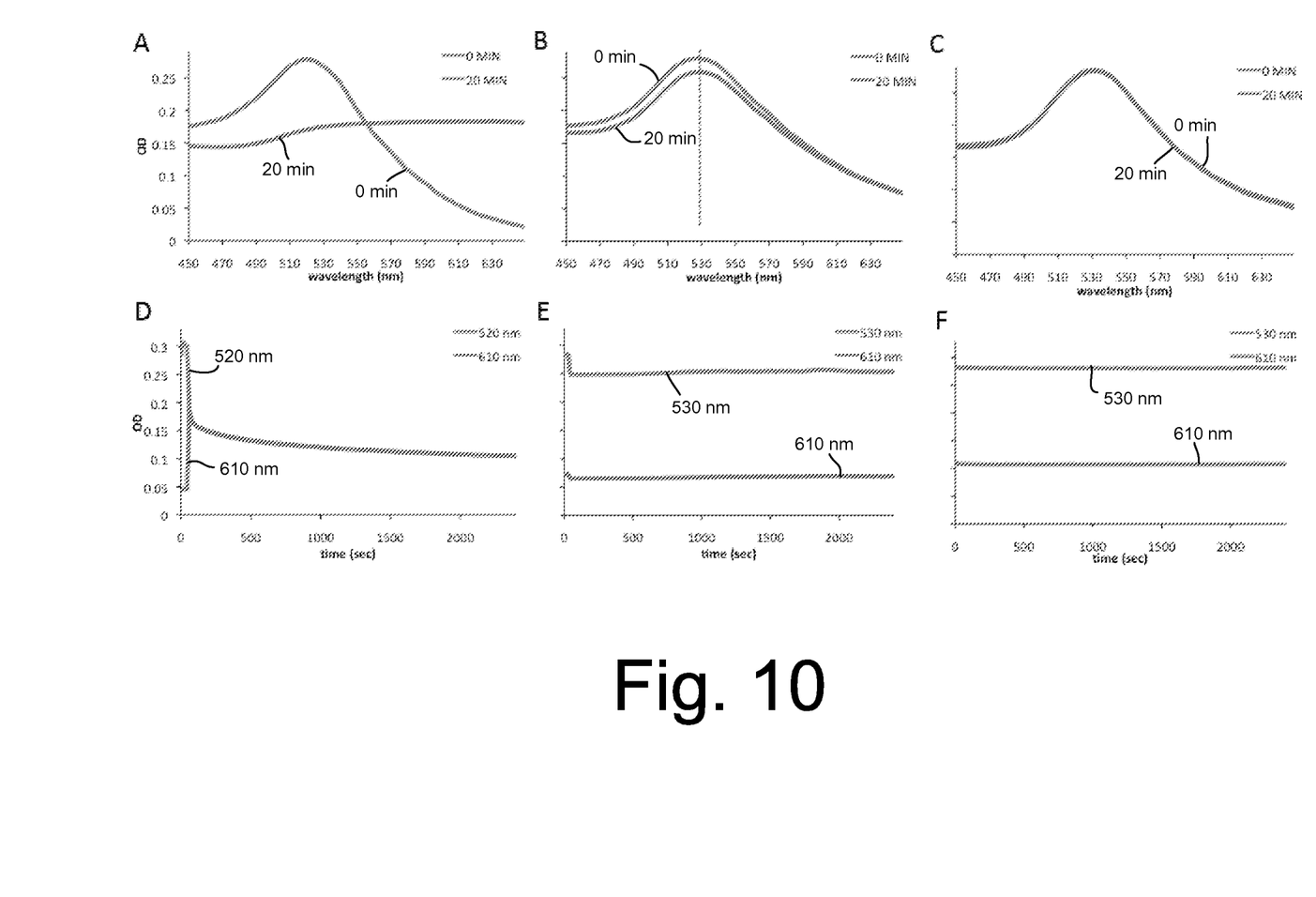
FIGS. 10A-10F are graphs of the stability of AuMN-DTTC compared to AuNP under various conditions.

Stability of the multifunctional contrast agent in biological conditions is important because the agent should remain relatively stable from injection though imaging. Referring now to FIGS. 10A through 10F, the stability of AuMN-DTTC is compared to that of AuNP at in various conditions. FIGS. 10A through 10C illustrate before and after absorbance spectra of AuNP in 0.4 M NaCl and 1×PBS (phosphate buffered saline), AuMN-DTTC in 0.4 M NaCl and 1×PBS, and AuMN-DTTC in fetal bovine serum, respectively. The change in optical density of selected wavelengths (520 nm and 610 nm) over time is illustrated in FIGS. 10D through 10F, with the conditions of FIG. 10A corresponding to FIG. 10D, FIG. 10B corresponding to FIG. 10E, and FIG. 10C corresponding to FIG. 10F.

FIGS. 10A and 10D illustrate the stability of the citrate-stabilized AuNP. FIG. 10A shows the absorbance spectrum of AuNP before and 20 minutes after the addition of 0.4 M NaCl and PBS (phosphate buffered saline). The AuNP aggregate in the presence of the 0.4 M NaCl and PBS, which is observed as a surface plasmon resonance shift from 520 nm to higher wavelengths.

Referring now to FIGS. 10B and 10E, under similar environmental conditions (i.e., 0.4 M NaCl and 1×PBS), AuMN-DTTC is protected against aggregation by the PEG coating. Therefore, an aggregation of the particles is not observed in the presence of 0.4 M NaCl and PBS. Likewise, FIGS. 10C and 10F illustrate the stability of AuMN-DTTC in fetal bovine albumin.

Having established stability under biological conditions, the following experiments were performed to establish that the synthesized probe was MRI, SERS (surface enhanced Raman spectroscopy), and CT active.

Figure 11:
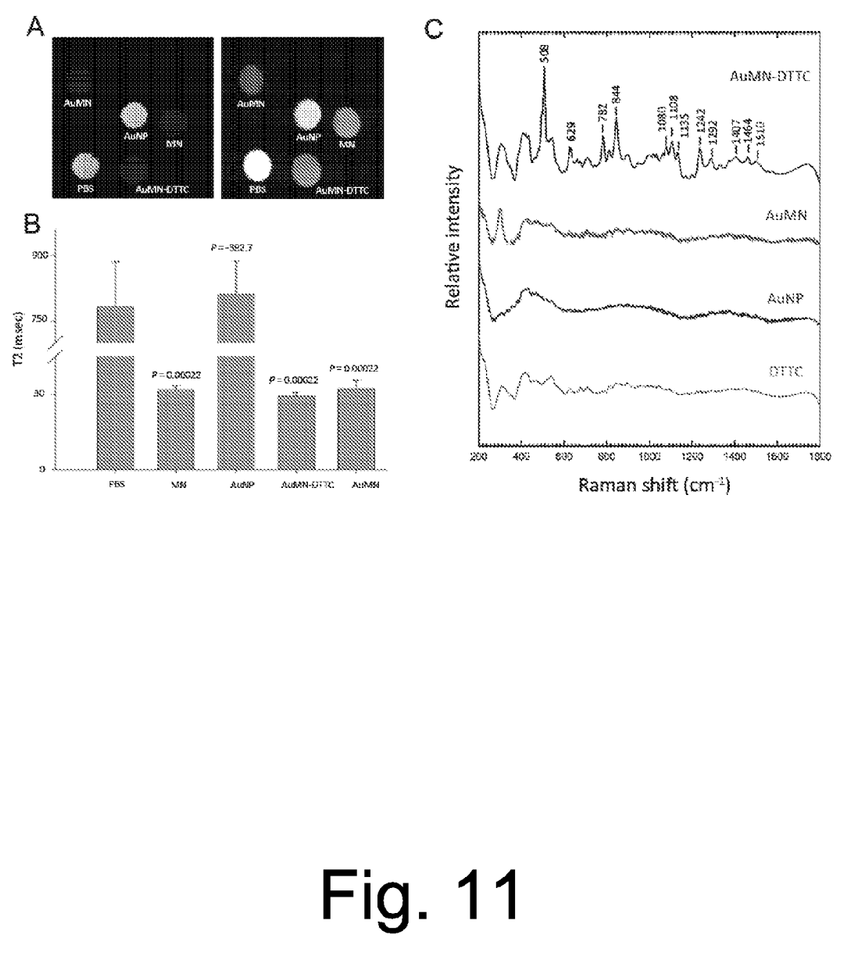
FIG. 11A is an in vitro T2 weighted MR image of AuMN-DTTC and the control probes in water.
FIG. 11B is a chart showing calculated T2 values.
FIG. 11C is a Raman spectra of AuMN-DTTC and control probes in water.

Referring to FIG. 11A, a T2 weighted MRI scan was performed on AuMN-DTTC along with the control probes in water. The T2 values from the images were also calculated and are shown in FIG. 11B. As seen in these figures, the AuMN-DTTC and AuMN has similar brightness as MN (the only difference of AuMN from AuMN-DTTC is that DTTC is not added during the synthesis of AuMN), but AuNP is significantly different than MN and close to the brightness of the blank solution PBS. This establishes that the AuMN-DTTC is valid as an MRI contrast agent in terms of signal capacity. The calculated T2 results also support this conclusion.

Tests were also performed to see if the synthesized AuMN-DTTC is SERS active. Referring to FIG. 11C, Raman spectra of AuMN-DTTC and control probes in water were collected. The control probes include AuMN (which does not include the Raman reporter DTTC dye), AuNP, and DTTC. As seen in FIG. 11C, AuMN-DTTC has identifiable peaks in its spectrum, whereas the other control samples such as AuMN and AuNP do not. These results suggest that AuMN-DTTC is SERS active.

Figure 12:
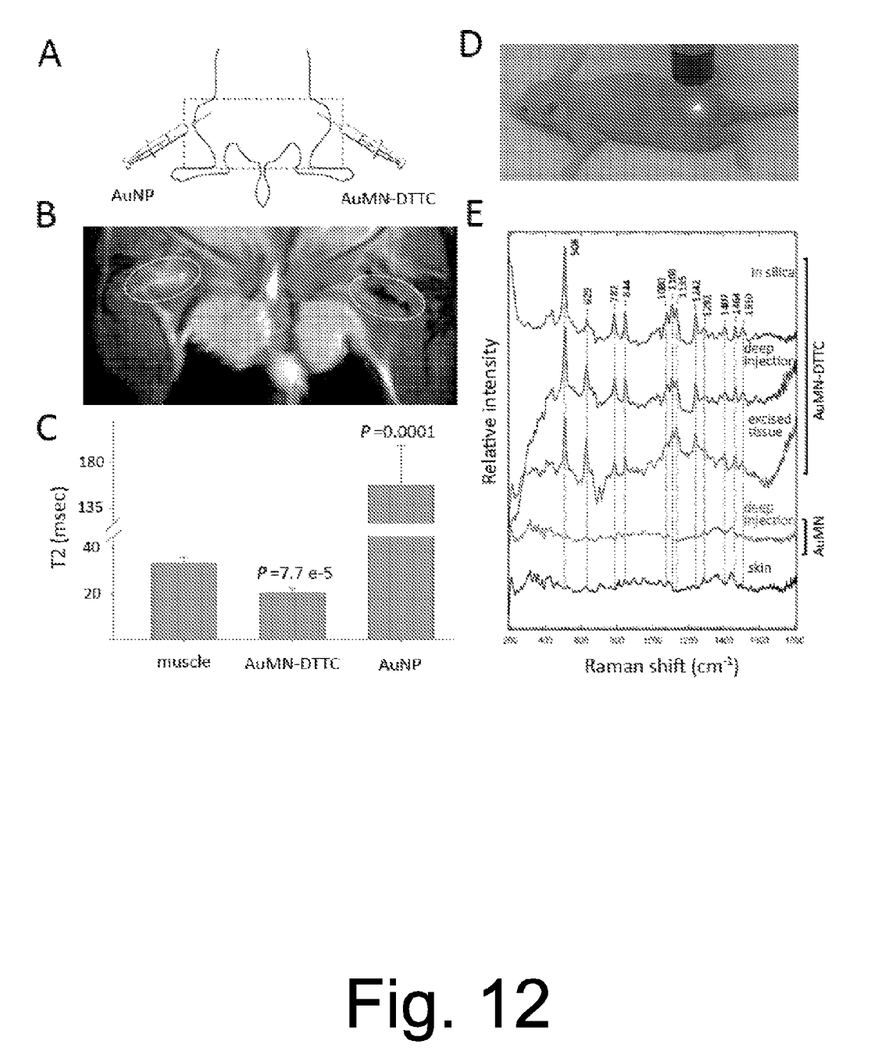
FIG. 12A is a schematic indicating the in vivo injection sites of AuNP and AuMN-DTTC in a test specimen.
FIG. 12B is a T2 weighted MR image of AuMN-DTTC and AuNP in the injected test specimen.
FIG. 12C is a chart showing calculated T2 values.
FIG. 12D is a photo of the specimen undergoing Raman spectroscopy.
FIG. 12E is a Raman spectra of AuMN-DTTC and control probes in deep muscle injection.

In vivo MRI and SERS experiments were performed in a test specimen. AuMN-DTTC was injected into the right gluteal muscle of a mouse and AuNP into the left gluteal muscle, as shown schematically in FIG. 12A. As seen in FIG. 12B, the AuMN-DTTC in the right muscle has a dark signal in comparison to the surrounding tissue and in comparison to the left muscle. As shown in FIG. 12C, T2 values were calculated on the image and the AuMN-DTTC injected tissue has a significantly lower T2 value compared to tissue injected with AuNP.

As shown in FIG. 12D, the SERS spectra in the injected areas were obtained from the living specimen. As seen in FIG. 12E, the tissue containing AuMN-DTTC has the same SERS peaks as AuMN-DTTC in silica. However, AuMN injected tissue or skin does not exhibit clearly identifiable SERS peaks. The tissue was also excised and monitored and SERS was observed in the excised tissue as well. These results indicate that the AuMN-DTTC contrast agent is not only MR active, but is also SERS active.

Figure 13:
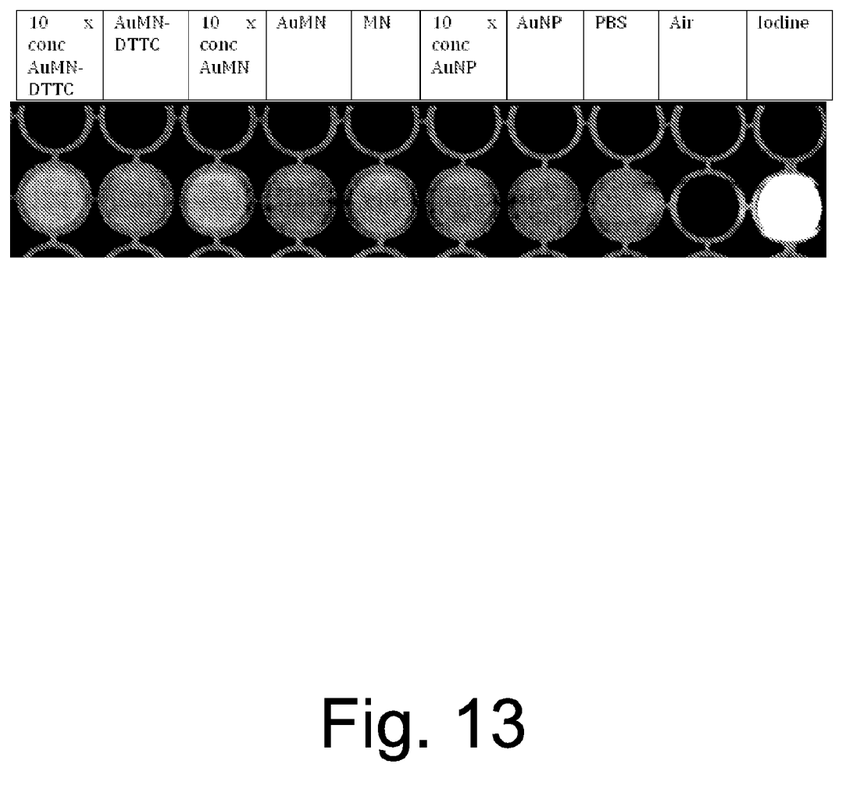
FIG. 13 is an image of in vitro CT values of AuMN-DTTC and the control probes.

In order to monitor if the compound creates change in CT signal due to gold content, a phantom of the AuMN-DTTC probes and control probes was made. The AuMN-DTTC was compared to PBS. As seen in FIG. 13, the 10× concentrated AuMN-DTTC has a CT signal higher than PBS but relatively lower than iodine, which is a CT contrast agent.

It should be appreciated that various other modifications and variations to the preferred embodiments can be made within the spirit and scope of the invention. Therefore, the invention should not be limited to the described embodiments. To ascertain the full scope of the invention, the following claims should be referenced. All patents, applications, and publications cited herein are incorporated by reference in their entirety for all purposes.

What is claimed is:

1. A method of forming gold-coated iron oxide nanoparticles, comprising:
   contacting dextran-coated iron oxide nanoparticles with a gold donating reagent in a citrate solution;
   wherein a gold shell is formed on each of the dextran-coated iron oxide particles to provide gold-coated iron oxide nanoparticles.

2. The method of claim 1, wherein the gold donating reagent is chloroauric acid.

3. The method of claim 1, further comprising:
   forming gold nanoparticles from chloroauric acid;
   depositing at least some of the gold nanoparticles onto a surface of the dextran-coated iron oxide nanoparticles to form gold nanoparticle conjugated iron oxide nanoparticles; and
   reducing additional gold chloride ions on the surface of the gold nanoparticle conjugated iron oxide nanoparticles to form the gold-coated iron oxide nanoparticles.

4. The method of claim 3, wherein hydroxylamine is used to reduce the additional gold chloride ions.

5. The method of claim 3, further comprising separating the gold nanoparticle conjugated iron oxide nanoparticle by magnetic column prior to reducing additional gold chloride ions on the surface of the gold nanoparticle conjugated iron oxide nanoparticle.

6. The method of claim 1, wherein the gold-coated iron oxide nanoparticles are clinically applicable and are substantially free of toxins.

7. The method of claim 1, wherein the gold-coated iron oxide nanoparticles are MRI active due to the iron oxide and are CT active due to an amount and morphology of gold surrounding the iron oxide.

8. The method of claim 1, further comprising functionalizing the gold-coated iron oxide nanoparticles with at least one of a Raman spectroscopy active dye and a targeting moiety.

9. A gold-coated iron oxide nanoparticle manufactured by the method of claim 1.

10. A nanoparticle comprising:
    an iron oxide core;
    a dextran layer surrounding the iron oxide core; and
    a gold coating formed on the dextran layer
    wherein the gold coating is a gold shell surrounding the dextran layer and the iron oxide.

11. The nanoparticle of claim 10, wherein the iron oxide core is superparamagnetic.

12. The nanoparticle of claim 10, wherein the nanoparticle is clinically applicable and is substantially free of toxins.

13. The nanoparticle of claim 10, wherein the nanoparticle has a diameter in a range of about 60 nanometers to about 120 nanometers.

14. The nanoparticle of claim 10, wherein the gold coating of the nanoparticle is adapted to be functionalized with targeting moieties.

15. The nanoparticle of claim 10, wherein the nanoparticle is adapted for use as a contrast agent.

16. The nanoparticle of claim 15, wherein the nanoparticle is adapted for use in a therapeutic application.

17. The nanoparticle of claim 10, wherein the gold coating is functionalized with at least one of a Raman spectroscopy active dye and a targeting moiety.

18. A method of imaging a subject, comprising:
    introducing a plurality of nanoparticles according to claim 9 into a subject; and
    performing at least two modes of imaging in the subject using the plurality of nanoparticles as a contrast agent for the at least two modes of imaging.

19. The method of claim 18, wherein one of the modes of imaging is magnetic resonance imaging.

20. The method of claim 18, wherein one of the modes of imaging is CT imaging.

21. The method of claim 18, wherein one of the modes of imaging employs Raman spectroscopy.

22. The method of claim 18, further comprising the step of applying an energy source to raise the temperature of the plurality of nanoparticles in the subject whereby a therapeutic treatment is provided to said subject.

23. A method of providing a therapeutic treatment to a subject, comprising:
    introducing a plurality of nanoparticles according claim 9 into a subject; and
    applying an energy source to raise the temperature of the plurality of nanoparticles in the subject whereby a therapeutic treatment is provided to said subject.

24. The method of claim 23, wherein the energy source is an alternating magnetic field.

25. The method of claim 23, wherein the energy source is an infrared light.

26. The method of claim 18, wherein the plurality of nanoparticles are manufactured according to the method of claim 1.

* * * * *